US012513442B2

(12) United States Patent
Picot et al.

(10) Patent No.: US 12,513,442 B2
(45) Date of Patent: Dec. 30, 2025

(54) MEDICAL DEVICE WITH AUDIO OUTPUT FOR USE IN A STERILE FIELD

(71) Applicant: Becton, Dickinson and Company, Franklin Lakes, NJ (US)

(72) Inventors: John Picot, Landing, NJ (US); Gary Ellerbusch, Nutley, NJ (US); Matthew Lee Kolb, Bloomingdale, NJ (US); Hong Zhu, Glen Rock, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 270 days.

(21) Appl. No.: 18/034,952

(22) PCT Filed: Nov. 2, 2021

(86) PCT No.: PCT/US2021/057673
§ 371 (c)(1),
(2) Date: May 2, 2023

(87) PCT Pub. No.: WO2022/098626
PCT Pub. Date: May 12, 2022

(65) Prior Publication Data

US 2024/0022844 A1 Jan. 18, 2024

Related U.S. Application Data

(60) Provisional application No. 63/108,925, filed on Nov. 3, 2020.

(51) Int. Cl.
*H04R 1/02* (2006.01)
*A61L 2/00* (2006.01)

(52) U.S. Cl.
CPC ................ *H04R 1/028* (2013.01); *A61L 2/00* (2013.01); *H04R 1/023* (2013.01); *A61L 2202/23* (2013.01)

(58) Field of Classification Search
CPC ........ H04R 1/028; H04R 1/023; H04R 7/045; H04R 1/44; A61L 2/00; A61L 2202/23
See application file for complete search history.

(56) References Cited

U.S. PATENT DOCUMENTS 6,021,208 A * 2/2000 Kin-Lung ........... B60R 11/0217 381/350
6,445,803 B1 * 9/2002 Boon ....................... H04R 9/06 381/423
2012/0082317 A1 * 4/2012 Pance .................... H04R 7/045 381/59

(Continued)

FOREIGN PATENT DOCUMENTS

CN 211511778 U * 9/2020 ........... A61B 5/0205
JP S52129932 U 10/1977

(Continued)

*Primary Examiner* — Oyesola C Ojo
(74) *Attorney, Agent, or Firm* — The Webb Law Firm

(57) ABSTRACT

A medical device with audio output for use in a sterile field may include a housing and an audio output device. The housing may include an interior surface and an exterior surface, the interior surface may define an interior space of the housing including the audio output device, and the interior space of the housing may be fluidically sealed from an external environment by the housing. The audio output device may include a speaker and/or an audio exciter.

17 Claims, 16 Drawing Sheets

(56) References Cited

U.S. PATENT DOCUMENTS

| | | | | |
|---|---|---|---|---|
| 2012/0095398 | A1 | 4/2012 | Fonacier et al. | |
| 2015/0237424 | A1 * | 8/2015 | Wilker | H04R 3/04 381/150 |
| 2018/0228259 | A1 | 8/2018 | Lipner et al. | |
| 2019/0037293 | A1 | 1/2019 | Kim | |
| 2019/0069056 | A1 * | 2/2019 | Yoon | H04R 1/023 |
| 2020/0045398 | A1 * | 2/2020 | Wu | H04R 1/025 |
| 2020/0154209 | A1 * | 5/2020 | Dinaburg | H04R 9/06 |
| 2022/0295162 | A1 * | 9/2022 | Chen | H04R 1/2888 |
| 2023/0254395 | A1 * | 8/2023 | Chen | H04R 1/02 455/569.1 |
| 2024/0022844 | A1 * | 1/2024 | Picot | H04R 7/045 |

FOREIGN PATENT DOCUMENTS

| | | | |
|---|---|---|---|
| JP | S59111386 | U | 7/1984 |
| JP | 20135936 | A | 1/2013 |
| JP | 201930006 | A | 2/2019 |

* cited by examiner

MEDICAL DEVICE WITH AUDIO OUTPUT FOR USE IN A STERILE FIELD

CROSS-REFERENCE TO RELATED APPLICATIONS

This application is the United States national phase of International Application No. PCT/US2021/057673 filed Nov. 2, 2021, and claims priority to U.S. Provisional Application Ser. No. 63/108,925, entitled "Medical Device with Audio Output for Use in a Sterile Field", filed Nov. 3, 2020, the entire disclosures of which are hereby incorporated by reference in their entirety.

BACKGROUND

1. Field

The present disclosure relates generally to a medical device and, in some non-limiting embodiments or aspects, to a medical device with audio output for use in a sterile field.

2. Technical Considerations

For a medical device that is used in a sterile field to be reused, the device must be cleanable using a solution containing bleach. In order to protect electrical components of the device, the device may prevent fluids from ingress into an interior of the device including the electrical components.

Medical devices, and particularly medical devices used in a sterile field, such as an operating room, and/or the like, are typically designed without small openings or crevices where material can accumulate and make disinfecting the device more difficult. Typical electronic devices, such as smartphones, tablets, and/or the like, include small holes or grates for speakers to provide audio output to a user. These holes or grates provide a location where material can accumulate and be difficult to remove, thereby making disinfecting such devices more difficult.

SUMMARY

Accordingly, provided are improved systems, devices, products, apparatus, and/or methods for medical devices with audio output for use in a sterile field.

According to some non-limiting embodiments or aspects, provided is a medical device with audio output for use in a sterile field that includes a housing, a speaker cover, a speaker enclosure, and a speaker frame. The housing includes an interior surface and an exterior surface, the interior surface defining an interior space of the housing. The housing includes an opening to the interior space of the housing. The speaker cover is located in the opening of the housing, the housing and the speaker cover fluidically sealing the interior space of the housing from an external environment. The exterior surface of the housing is exposed to the external environment. The speaker enclosure is connected the housing. The speaker frame includes a speaker driver and is located in the interior space of the housing between the speaker cover and the speaker enclosure, the interior space of the housing including the speaker frame including speaker driver being fluidically sealed from the external environment by the housing and the speaker cover.

According to some non-limiting embodiments or aspects, provided is a medical device with audio output for use in a sterile field that includes a housing and an audio exciter. The housing includes an interior surface and an exterior surface, the interior surface defining an interior space of the housing, and the interior space of the housing being fluidically sealed from an external environment by the housing. The audio exciter is connected to the interior surface of the housing and fluidically sealed from the external environment by the housing.

Further embodiments or aspects are set forth in the following numbered clauses:

Clause 1. A medical device with audio output for use in a sterile field, comprising: a housing including an interior surface and an exterior surface, wherein the interior surface defines an interior space of the housing, and wherein the housing includes an opening to the interior space of the housing; a speaker cover in the opening of the housing, wherein the housing and the speaker cover fluidically seal the interior space of the housing from an external environment, and wherein the exterior surface of the housing is exposed to the external environment; a speaker enclosure connected the housing; and a speaker frame including a speaker driver in the interior space of the housing between the speaker cover and the speaker enclosure, wherein the interior space of the housing including the speaker frame including speaker driver is fluidically sealed from the external environment by the housing and the speaker cover.

Clause 2. The medical device of clause 1, wherein the speaker enclosure includes a base and a sidewall extending from and surrounding the base, wherein the base includes a projection extending from the base in a same direction as the sidewall, and wherein the speaker frame including the speaker driver is connected to the projection.

Clause 3. The medical device of any of clauses 1 and 2, wherein the base includes a hole.

Clause 4. The medical device of any of clauses 1-3, further comprising: an adhesive foam between the speaker frame and the projection.

Clause 5. The medical device of any of clauses 1-4, wherein the speaker cover includes a central portion surrounded by a flange, wherein the flange forms a fluid tight seal with the exterior surface of the housing.

Clause 6. The medical device of any of clauses 1-5, wherein the flange is connected to the exterior surface of the housing via an adhesive to form the fluid tight seal.

Clause 7. The medical device of any of clauses 1-6, wherein the flange includes a flexible material, wherein the speaker frame includes a plurality of tabs of rigid material more rigid than the flexible material and extending from the frame, wherein an underside of the flange is connected to the exterior surface of the housing, and wherein a top surface of the plurality of tabs is connected to the interior surface of the housing.

Clause 8. The medical device of any of clauses 1-7, wherein the speaker enclosure is integrally formed with the housing.

Clause 9. The medical device of any of clauses 1-8, wherein the speaker cover is directly connected to the speaker enclosure.

Clause 10. The medical device of any of clauses 1-9, wherein the housing includes a flat-panel display, and wherein flat-panel display forms a portion of the exterior surface of the housing.

Clause 11. The medical device of any of clauses 1-10, further comprising: a flow sensor.

Clause 12. A medical device with audio output for use in a sterile field, comprising: a housing including an interior surface and an exterior surface, wherein the interior surface defines an interior space of the housing, and wherein the interior space of the housing is fluidically sealed from an external environment by the housing; and an audio exciter connected to the interior surface of the housing and fluidically sealed from the external environment by the housing.

Clause 13. The medical device of clause 12, wherein a portion of the exterior surface of the housing opposite a portion of the interior surface of the housing to which the audio exciter is connected includes a plurality of raised portions spaced apart from one another and extending from the exterior surface of the housing.

Clause 14. The medical device of any of clauses 12 and 13, wherein the audio exciter is connected to the interior surface of the housing between the plurality of raised portions extending from the exterior surface of the housing.

Clause 15. The medical device of any of clauses 12-14, wherein the plurality or raised portions includes at least three raised portions.

Clause 16. The medical device of any of clauses 12-15, wherein a portion of the interior surface of the housing to which the audio exciter is connected includes a recess such that a thickness of the housing between the interior surface and the exterior surface at the recess is less than the thickness of the housing surrounding the recess.

Clause 17. The medical device of any of clauses 12-16, wherein the recess is located between the plurality of raised portions extending from the exterior surface of the housing.

Clause 18. The medical device of any of clauses 12-17, wherein the housing includes a flat-panel display, and wherein the portion of the interior surface of the housing to which the audio exciter is connected is directly opposite another portion of the interior surface of the housing including the flat-panel display.

Clause 19. The medical device of any of clauses 12-18, wherein the housing includes a flat-panel display, and wherein the audio exciter is connected to a portion of the interior surface of the housing including the flat-panel display.

Clause 20. The medical device of any of clauses 12-19, further comprising: a flow sensor.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of limits. As used in the specification and the claims, the singular form of "a," "an," and "the" include plural referents unless the context clearly dictates otherwise.

BRIEF DESCRIPTION OF THE DRAWINGS

Additional advantages and details of embodiments or aspects of the present disclosure are explained in greater detail below with reference to the exemplary embodiments that are illustrated in the accompanying schematic figures, in which:

FIG. 1I is perspective views of non-limiting embodiments or aspects of a speaker cover;

DETAILED DESCRIPTION

Figure 1A:
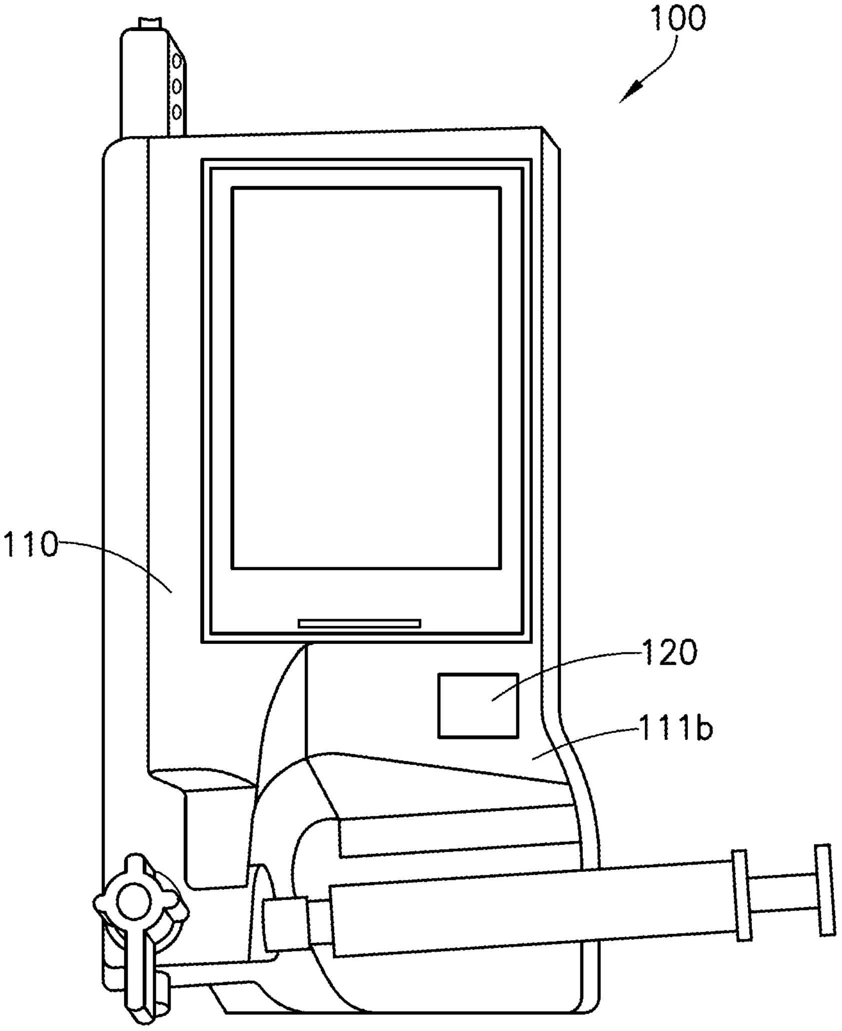
FIG. 1A is a perspective view of non-limiting embodiments or aspects of a medical device with audio output for use in a sterile field.
Figure 1B:
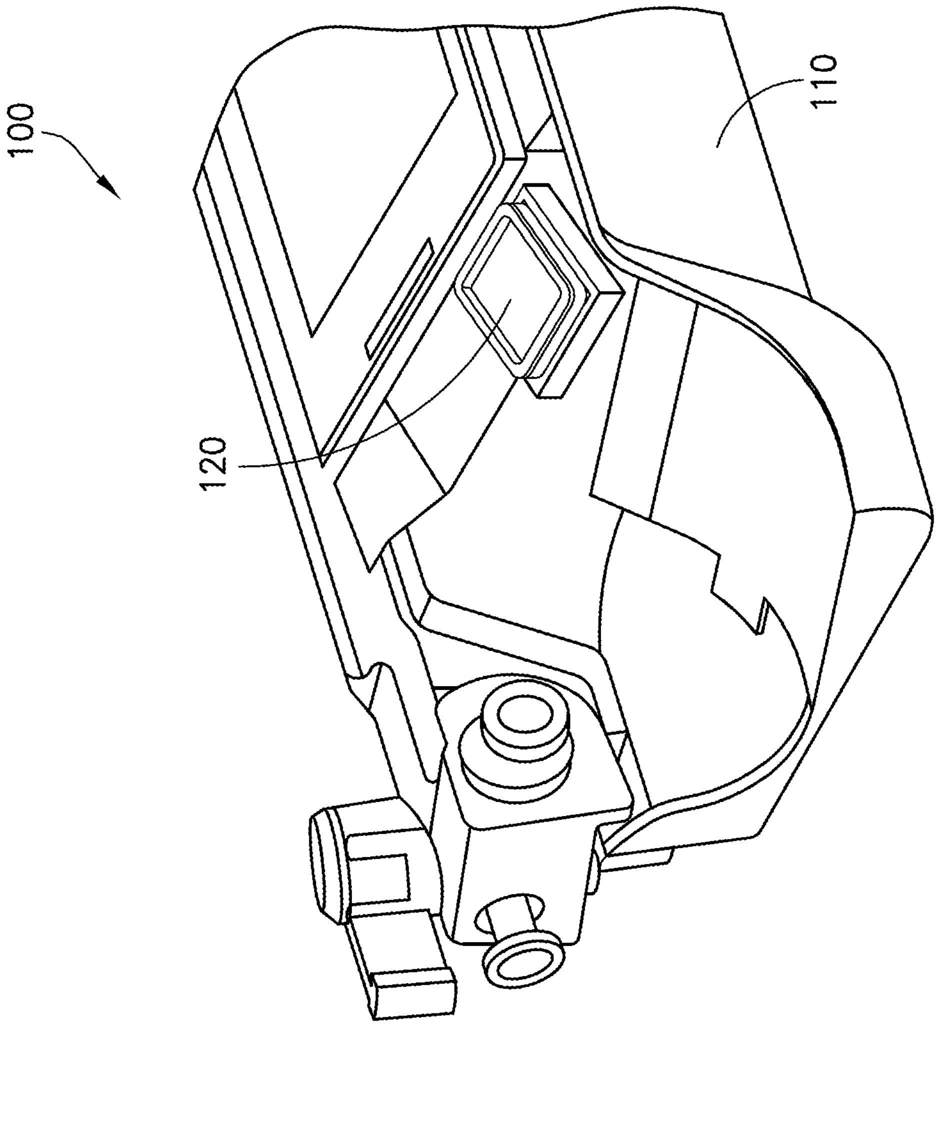
FIG. 1B is a perspective view of non-limiting embodiments or aspects of a medical device with audio output for use in a sterile field.
Figure 1C:
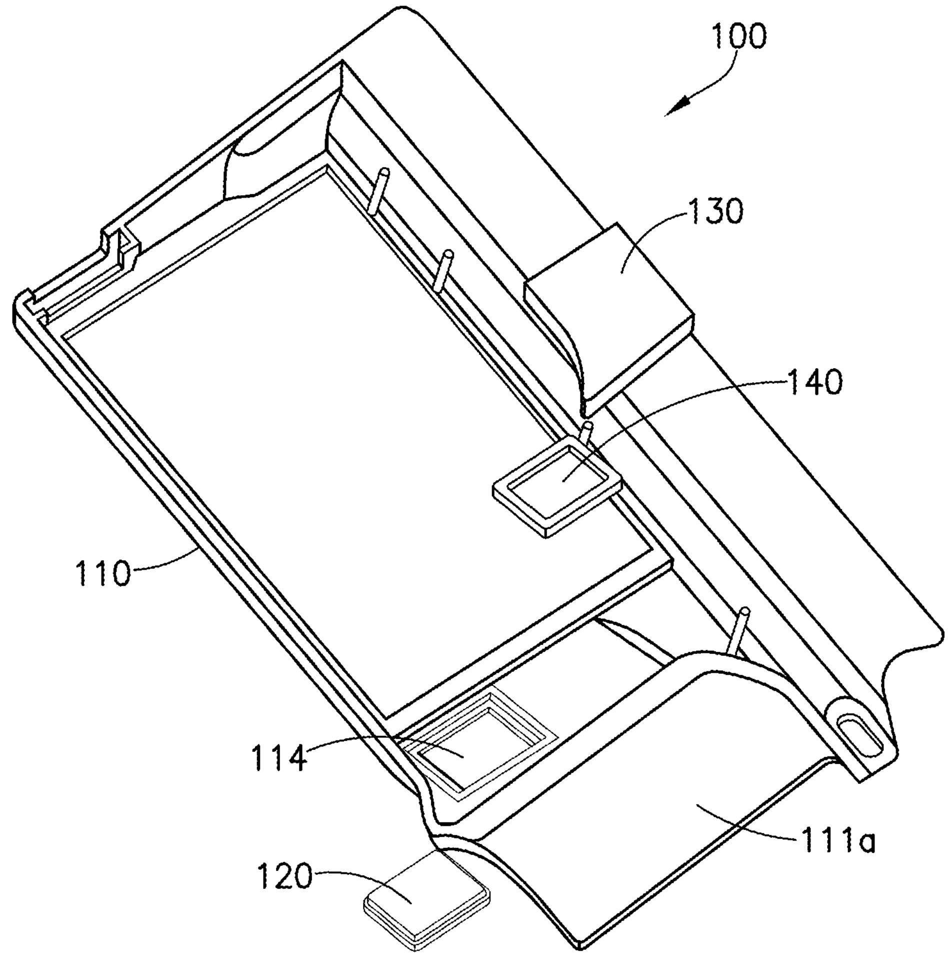
FIG. 1C is an exploded perspective view of non-limiting embodiments or aspects of components of a medical device with audio output for use in a sterile field.
Figure 1D:
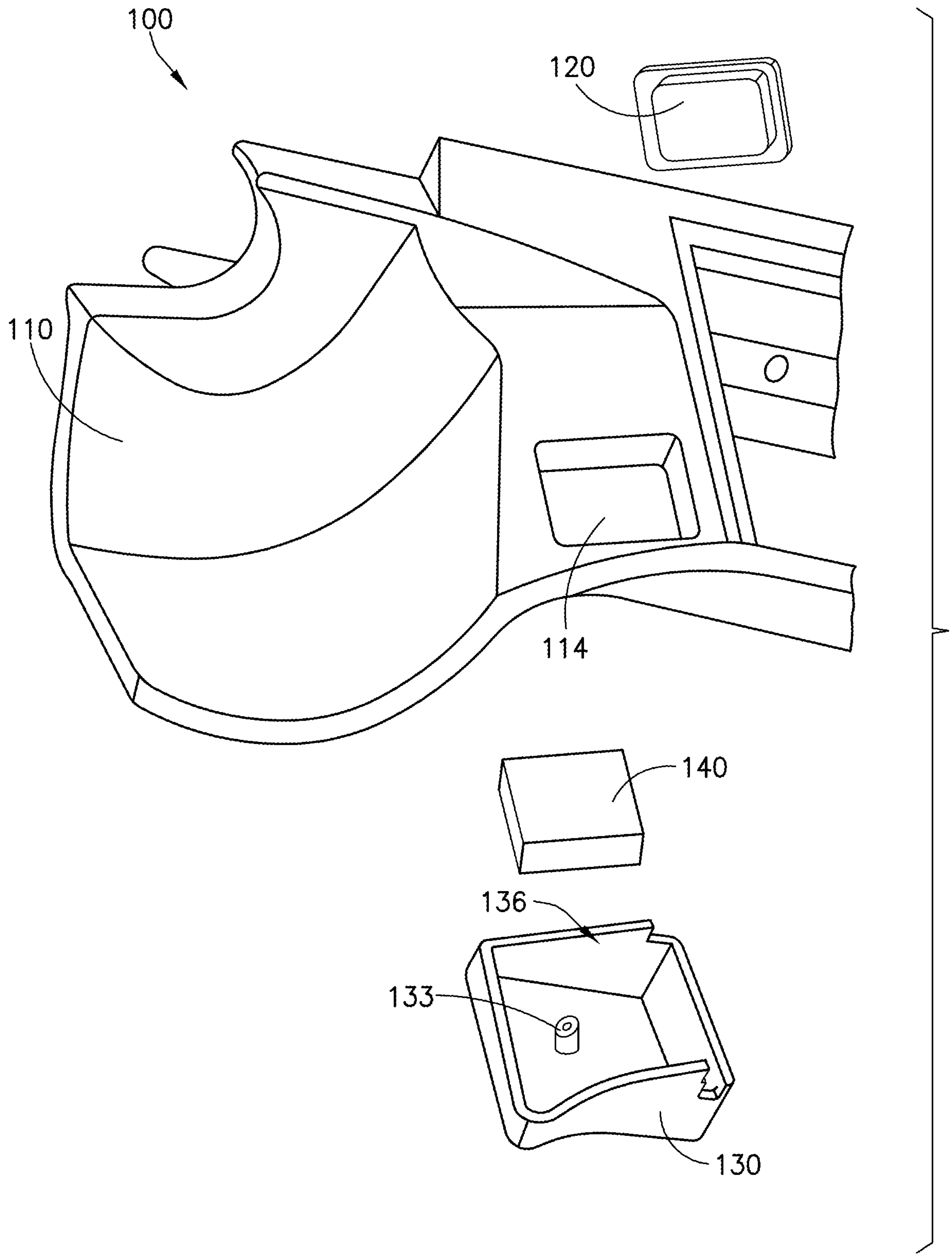
FIG. 1D is an exploded perspective view of non-limiting embodiments or aspects of components of a medical device with audio output for use in a sterile field.
Figure 1E:
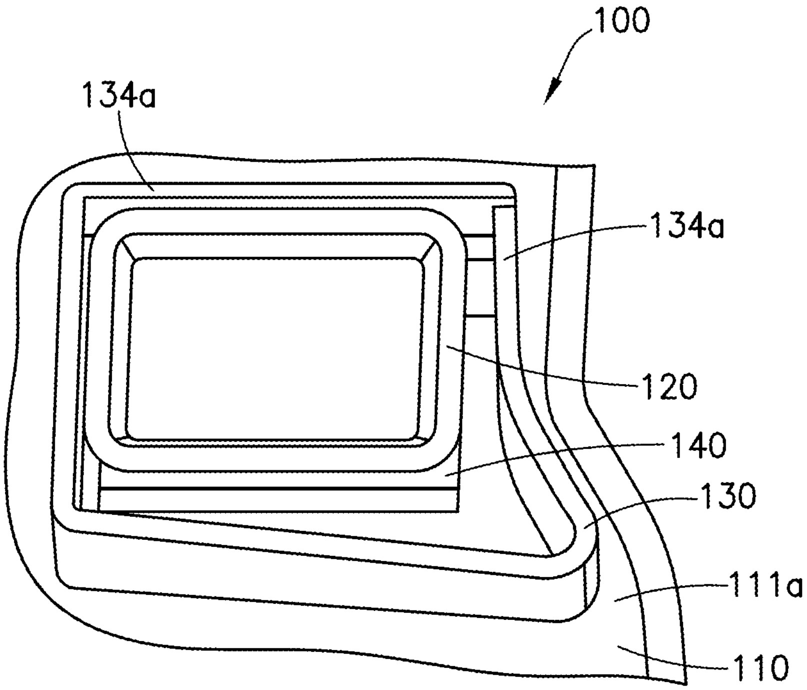
FIG. 1E is a perspective view of non-limiting embodiments or aspects of components of a medical device with audio output for use in a sterile field.
Figure 1F:
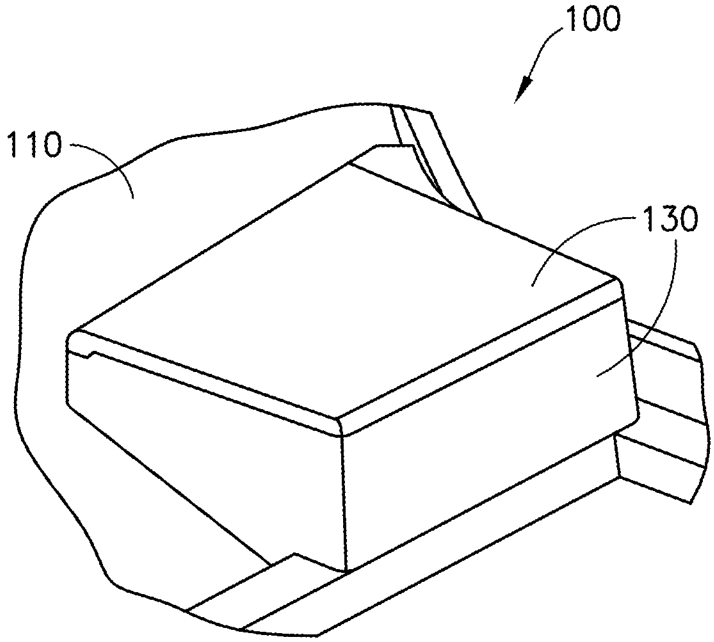
FIG. 1F is a perspective view of non-limiting embodiments or aspects of components of a medical device with audio output for use in a sterile field.
Figure 1G:
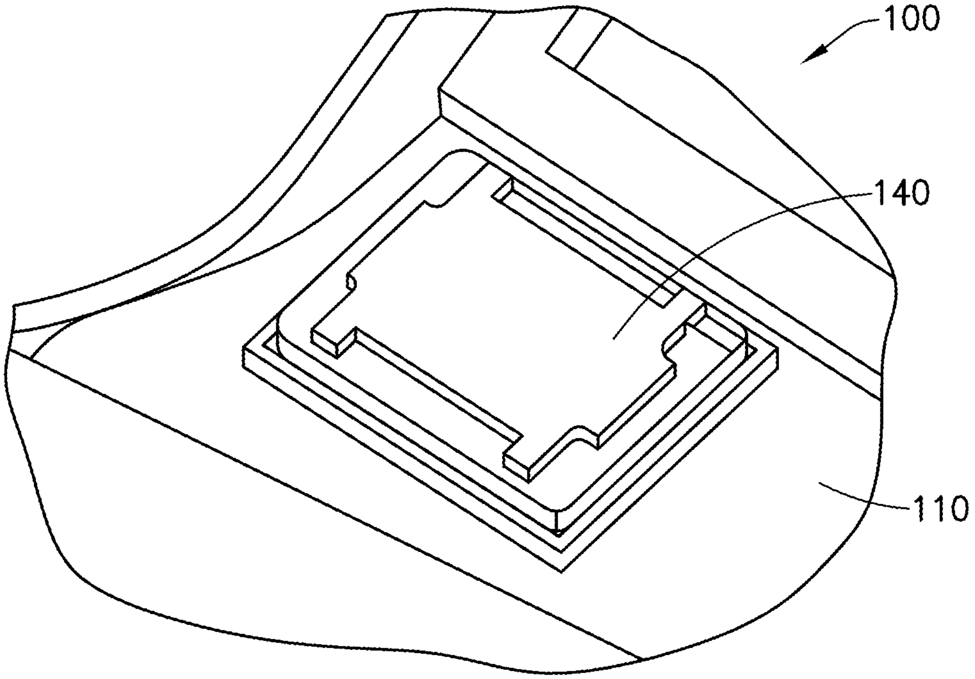
FIG. 1G is a perspective view of non-limiting embodiments or aspects of components of a medical device with audio output for use in a sterile field.
Figure 1H:
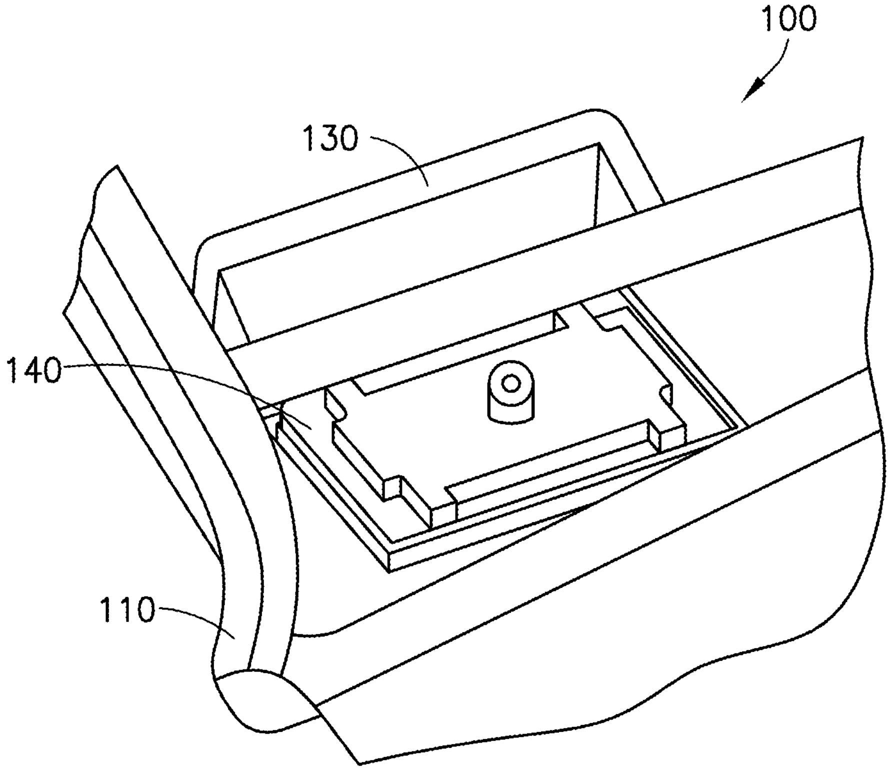
FIG. 1H is a perspective view of non-limiting embodiments or aspects of components of a medical device with audio output for use in a sterile field.
Figure 11:
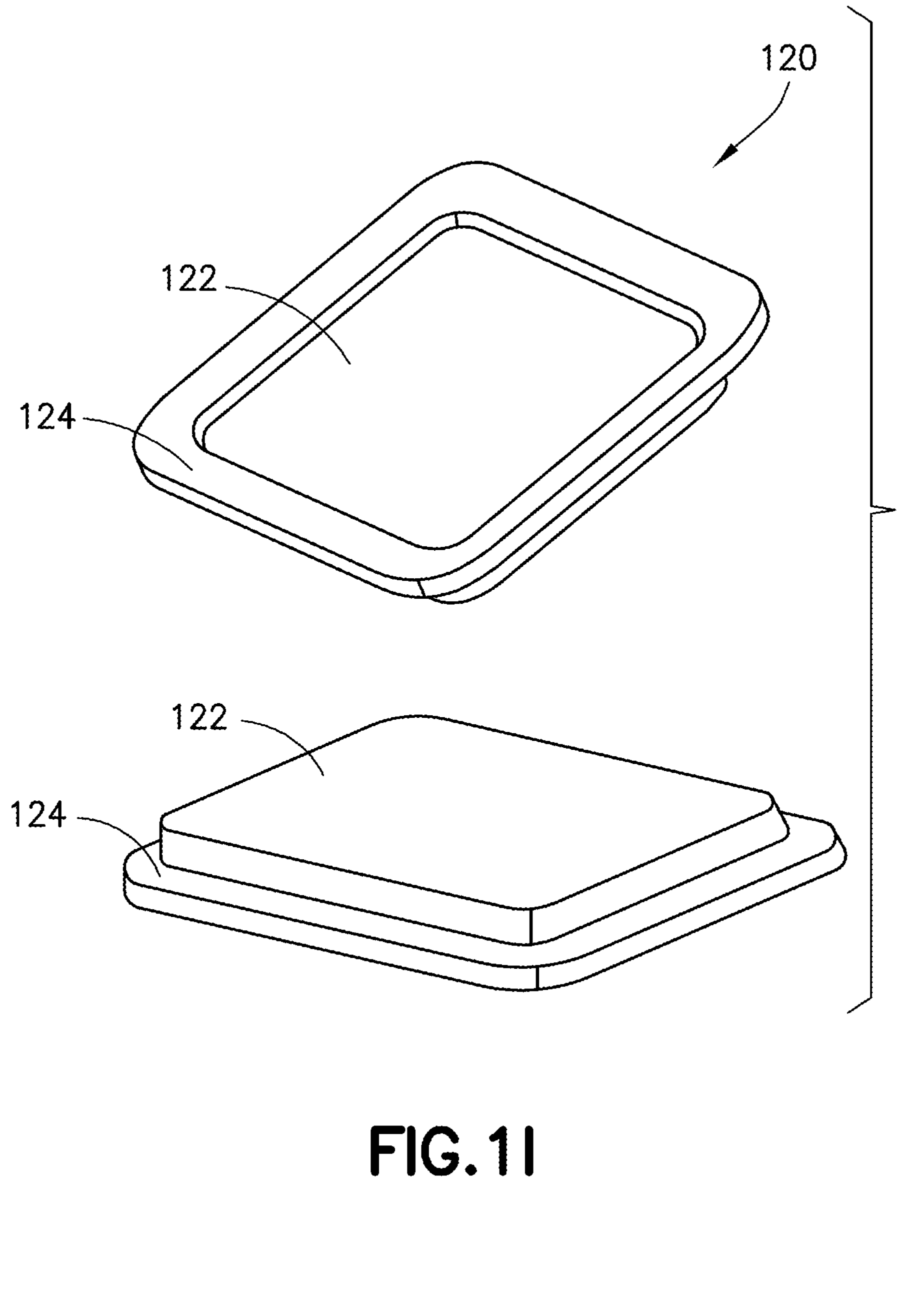
Figure 1J:
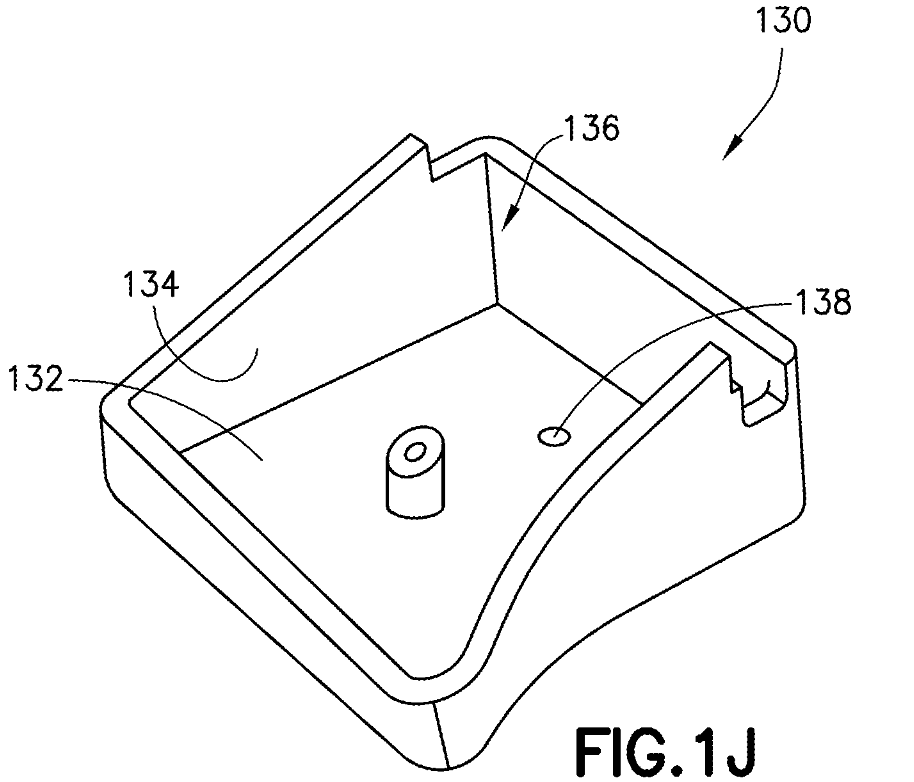
FIG. 1J is a perspective view of non-limiting embodiments or aspects of a speaker enclosure.
Figure 1K:
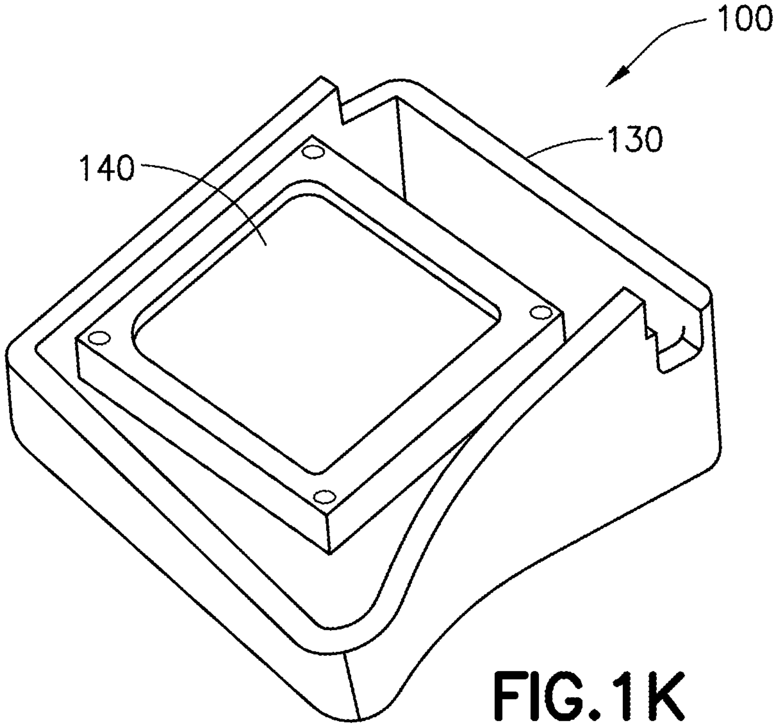
FIG. 1K is a perspective view of non-limiting embodiments or aspects of components of a medical device with audio output for use in a sterile field.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms “upper”, “lower”, “right”, “left”, “vertical”, “horizontal”, “top”, “bottom”, “lateral”, “longitudinal”, and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting. All numbers and ranges used in the specification and claims are to be understood as being modified in all instances by the term “about”. By “about” is meant plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or sub-ratios subsumed therein. For example, a stated range or ratio of “1 to 10” should be considered to include any and all subranges or sub-ratios between (and inclusive of) the minimum value of 1 and the maximum value of 10; that is, all subranges or sub-ratios beginning with a minimum value of 1 or more and ending with a maximum value of 10 or less. The ranges and/or ratios disclosed herein represent the average values over the specified range and/or ratio.

The terms “first”, “second”, and the like are not intended to refer to any particular order or chronology, but refer to different conditions, properties, or elements.

No aspect, component, element, structure, act, step, function, instruction, and/or the like used herein should be construed as critical or essential unless explicitly described as such. Also, as used herein, the articles “a” and “an” are intended to include one or more items, and may be used interchangeably with “one or more” and “at least one.” Furthermore, as used herein, the term “set” is intended to include one or more items (e.g., related items, unrelated items, a combination of related and unrelated items, etc.) and may be used interchangeably with “one or more” or “at least one.” Where only one item is intended, the term “one” or similar language is used. Also, as used herein, the terms “has,” “have,” “having,” or the like are intended to be open-ended terms. Further, the phrase “based on” is intended to mean “based at least in partially on” unless explicitly stated otherwise.

As used herein, the terms “communication” and “communicate” refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other even though the data transmitted may be modified, processed, relayed, and/or routed between the first and second unit. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

As used herein, the term “computing device” or “computer device” may refer to one or more electronic devices that are configured to directly or indirectly communicate with or over one or more networks. The computing device may be a mobile device, a desktop computer, or the like. Furthermore, the term “computer” may refer to any computing device that includes the necessary components to receive, process, and output data, and normally includes a display, a processor, a memory, an input device, and a network interface. An “application” or “application program interface” (API) refers to computer code or other data sorted on a computer-readable medium that may be executed by a processor to facilitate the interaction between software components, such as a client-side front-end and/or server-side back-end for receiving data from the client. An “interface” refers to a generated display, such as one or more graphical user interfaces (GUIs) with which a user may interact, either directly or indirectly (e.g., through a keyboard, mouse, touchscreen, etc.).

Figure 1L:
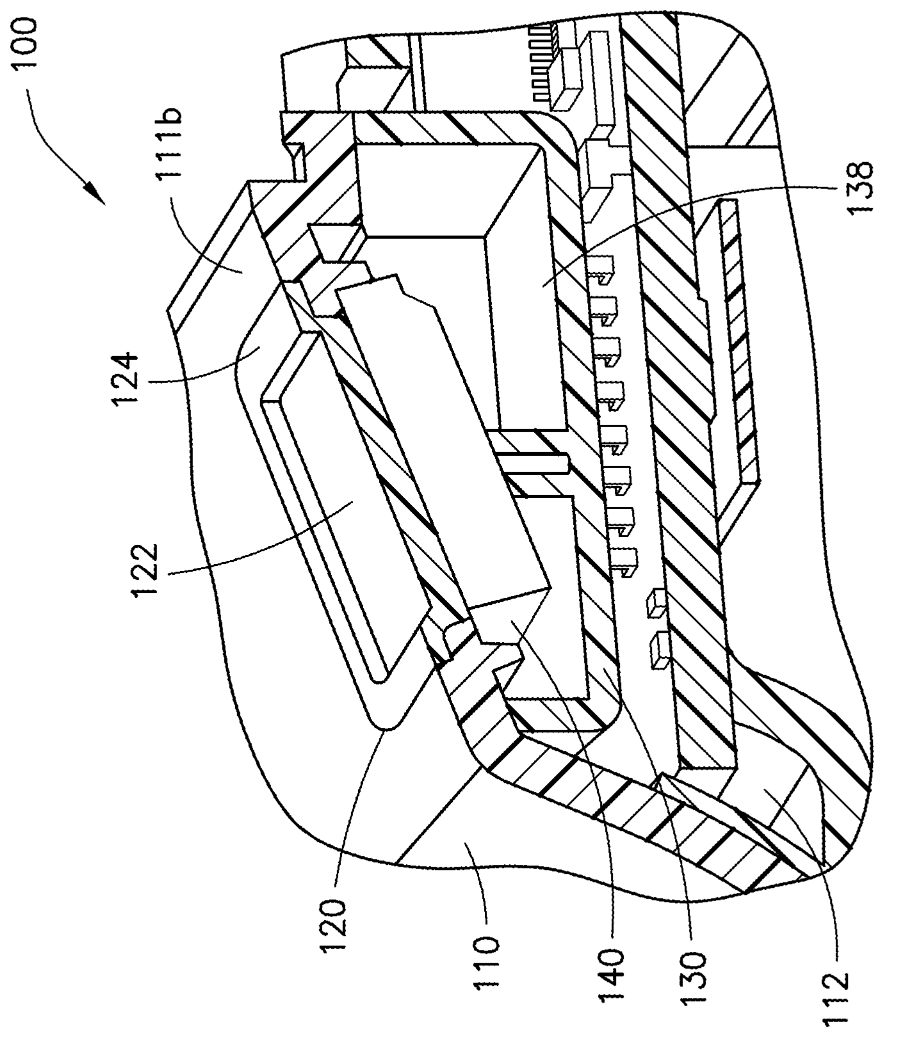
FIG. 1L is a cut-away view of non-limiting embodiments or aspects of components of a medical device with audio output for use in a sterile field.
Figure 1M:
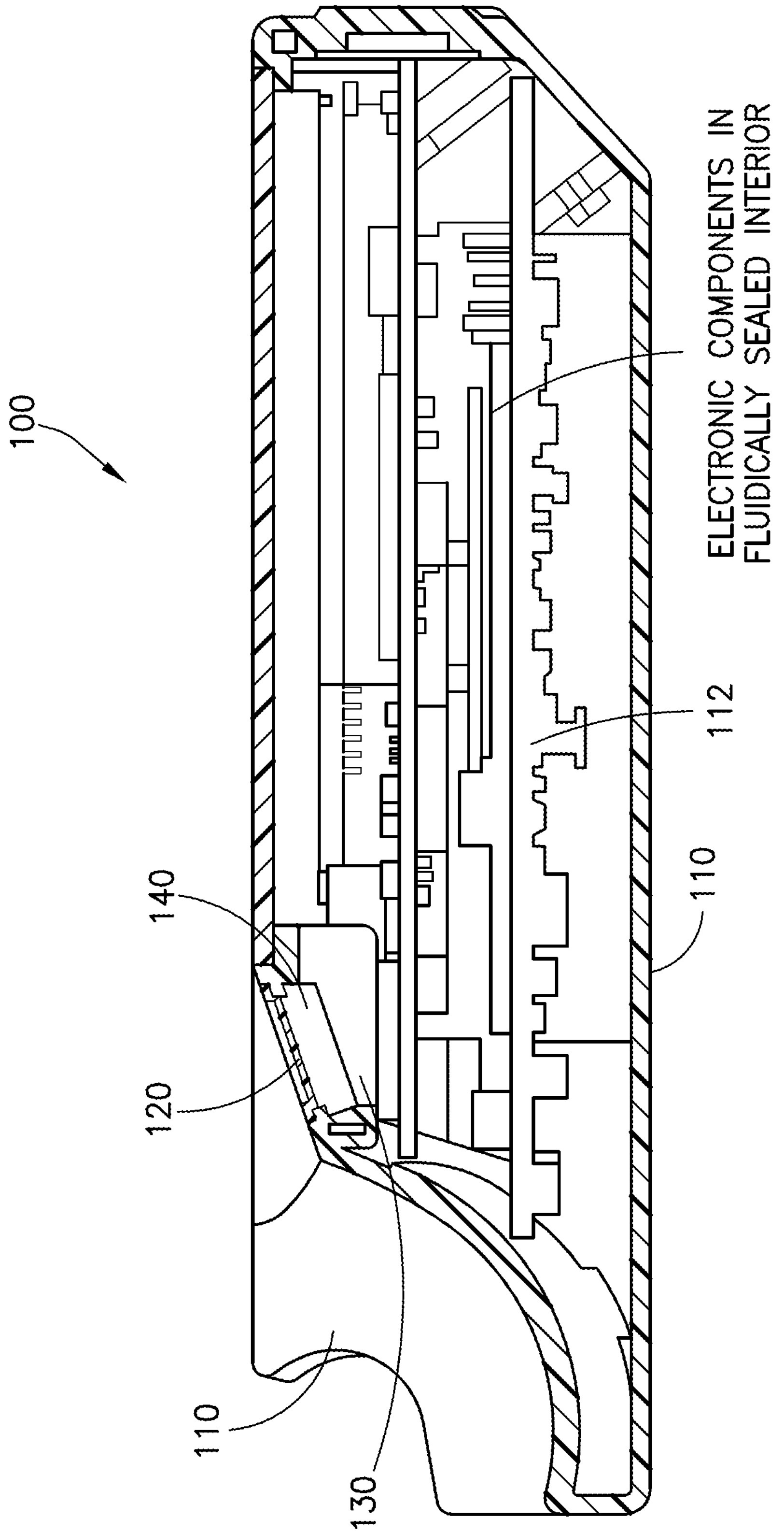
FIG. 1M is a cut-away view of non-limiting embodiments or aspects of a medical device with audio output for use in a sterile field.
Figure 1N:
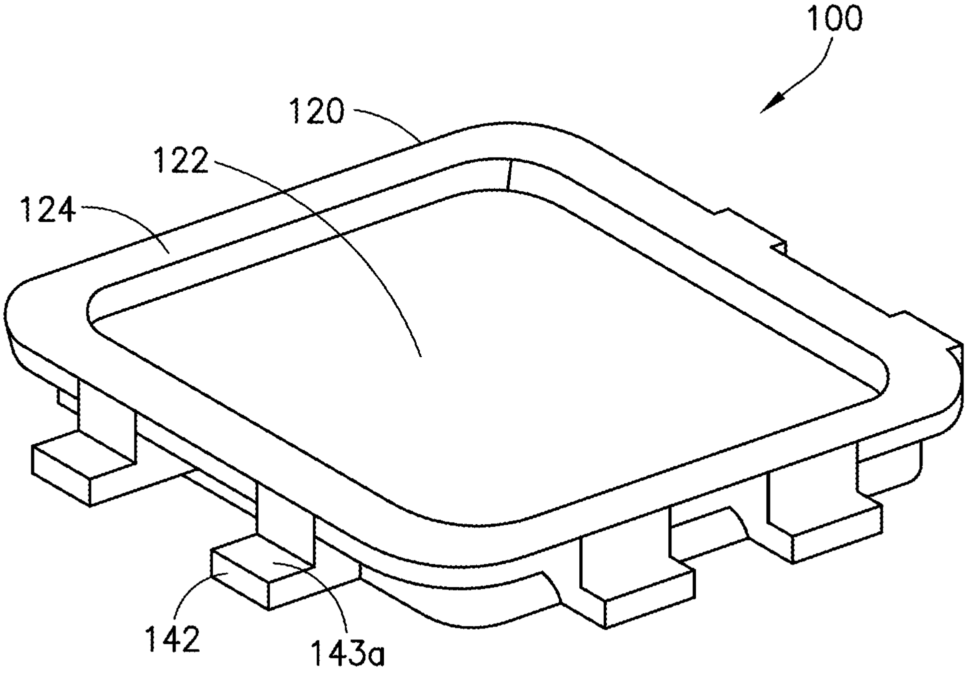
FIG. 1N is a perspective view of non-limiting embodiments or aspects of a speaker cover.
Figure 1O:
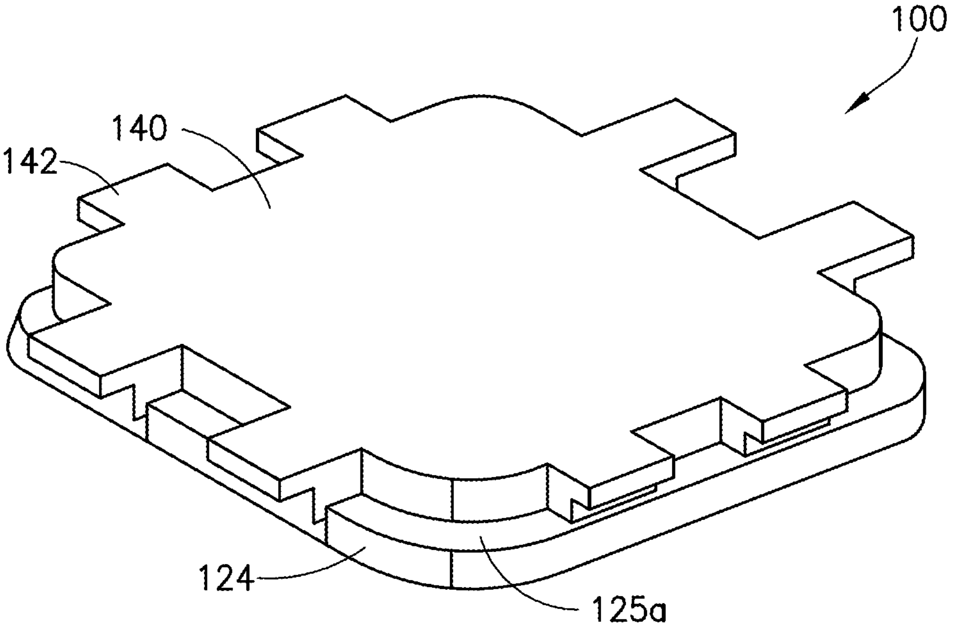
FIG. 1O is a perspective view of non-limiting embodiments or aspects of a speaker cover.

Referring to FIGS. 1A-1O, medical device 100 may include housing 110, speaker cover 120, speaker enclosure 130, and/or speaker frame 140. In some non-limiting embodiments or aspects, medical device 100 may include a flow sensor configured to measure one or more parameters associated with a fluid provided from a syringe and/or delivered to a patient. For example, medical device 100 may include, be included in, and/or formed by a flow sensor, a flow sensor base of a flow sensor system, and/or one or more components thereof, such as the flow sensor system disclosed in U.S. Pat. No. 9,970,794, which is hereby incorporated by reference in its entirety.

Housing 110 may include an interior **111*a* surface and an exterior surface 111*b*. Interior surface 111*a* may define an interior space 112 of housing 110. Housing 110 may include an opening 114 to interior space 112 of housing 110. In some non-limiting embodiments or aspects, housing 110 may include flat-panel display 116. For example, flat-panel display 116 may form a portion of exterior surface 111*b* of housing 110**.

Speaker cover 120 may include silicone, ethylene propylene diene monomer (EDPM), Thermoplastic Polyester Elastomer (TPE), or any combination thereof. Speaker cover 120 may be located in opening 114 of housing 110. For example, housing 110 and speaker cover 120 may fluidically seal interior space 112 of housing 110 from an external environment. As an example, exterior surface 111*a* may be exposed to the external environment, while interior space 112 and components (e.g., electronic components, such as a processor, a memory, a bus, a wireless communication device, wiring, and/or the like, speaker frame 140, a speaker driver, speaker enclosure 130, etc.) located in interior space 112 are sealed off from exposure to any fluids and/or gases that exterior surface 111*a* may be exposed to in the external environment.

In some non-limiting embodiments or aspects, speaker cover 120 may include central portion 122 surrounded by flange 124. For example, as shown in FIGS. 1I and 1L, flange 124 may form a fluid tight seal (e.g., with an IPX2 rating, etc.) with a portion of exterior surface 111*b* of housing 110 surrounding opening 114 of housing 110. As an example, flange 124 may be connected to (e.g., directly connected to, etc.) the portion of exterior surface 111*b* of housing 110 surrounding opening 114 of housing 110 (e.g., via an adhesive, etc.) to form the fluid tight seal. In such an example, speaker cover 120 may be permanently secured to exterior surface 111*b* of housing 110 via a chemical connection, a mechanical connection, an adhesive connection, or any combination thereof.

In some non-limiting embodiments or aspects, as shown, for example, in FIGS. 1N and 1O, flange 124 may include a flexible material, speaker frame 140 may include a plurality of tabs 142 of rigid material more rigid than the flexible material of flange 124 and extending from speaker frame 140. For example, an underside 125*a* of flange 124 may be connected to exterior surface 111*b* of housing 110 (e.g., to the portion of exterior surface 111*b* of housing 110 surrounding opening 114 of housing 110, etc.), and a top surface 143*a* of the plurality of tabs 142 may be connected to interior surface 111*a* of housing 110.

Speaker enclosure 130 may be connected to (e.g., directly connected to, etc.) housing 110. For example, speaker enclosure 130 may include base 132 and sidewall 134 extending from and surrounding base 132. As an example, a top surface 134*a* of sidewall 134 may be connected to interior surface 111*a* of housing 110 surrounding opening 114 of housing 110. Base 132 and sidewall 134 may define an interior area 136 of speaker enclosure 130. Base 132 may include opening or hole 138. For example, interior area 136 of speaker enclosure 130 may be in fluid communication with interior space 112 of housing 110 via opening or hole 138.

In some non-limiting embodiments or aspects, base 132 of speaker enclosure 130 may include projection 133 (e.g., a rod, a mechanical boss, etc.) extending from base 132 in a same direction as sidewall 134 and/or surrounded by sidewall 134. For example, speaker frame 140 including the speaker driver may be connected to (e.g., directly connected to, etc.) projection 133. As an example, adhesive foam 135 may be located between speaker frame 140 and projection 133, which may adhere speaker frame 140 to projection 133 and provide an element of cushioning or protection for speaker frame 140 including the speaker driver. Accordingly, projection 133 and/or adhesive foam 135 may provide a mount and registration to sufficiently secure and locate speaker frame 140 including the speaker drive to withstand drop tests, and/or the like.

In some non-limiting embodiments or aspects, speaker enclosure 130 may be integrally formed with housing 110. In some non-limiting embodiments or aspects, speaker cover 120 may be directly connected to and/or integrally formed with speaker enclosure 130.

Speaker frame 140 may include a speaker driver (not shown). Speaker frame 140 may be located in interior area 136 of speaker enclosure 130 within interior space 112 of housing 110 between speaker cover 120 and speaker enclosure 130. For example, speaker frame 140 may be connected to (e.g., directly connected to, etc.) speaker cover 120 and/or projection 133 (and/or adhesive 135). As an example, interior space 112 of housing 110 including interior area 136 of speaker enclosure 130 that includes speaker frame 140 including the speaker driver may be fluidically sealed from the external environment by housing 110 and speaker cover 120. In some non-limiting embodiment or aspects, speaker frame 140 including the speaker drive may include the AS01506MS-SP15-WP-R speaker manufactured by PUI Audio, Inc.

In some non-limiting embodiments or aspects, interior area 135 defined by speaker enclosure 130, housing 110, and/or speaker cover 120 may provide a baffle box or sealed air chamber with a volume of about 1 cc (1,0000 $mm^3$), a recess in speaker cover 120 may provide a thickness of 1 mm over central portion 122 of speaker cover 120, hole 138 may provide a pressure equalization hole of about 0.1-0.15 mm Ø, which may improve performance of the speaker above 1 kHz and enable the speaker to produce ≥70 dBA @ 1 meter per typical operating room requirements for medical devices. In some non-limiting embodiments or aspects, speaker enclosure 130 may provide a sealed (e.g., air tight, etc.) pass though for speaker wire connected to the speaker driver in speaker frame 140 and to the electrical components in interior 112 of housing 110. In some non-limiting embodiments or aspects, housing 110 may include curved thumb rest areas adjacent to speaker cover 120 to encourage a user to keep away from resting a finger on speaker cover 120 when held in a hand of the user.

Referring to FIGS. 2A-2I, medical device 200 may include housing 210 and audio exciter 250. In some non-limiting embodiments or aspects, medical device 100 may include a flow sensor configured to measure one or more parameters associated with a fluid provided from a syringe and/or delivered to a patient. For example, medical device 100 may include, be included in, and/or formed by a flow sensor, a flow sensor base of a flow sensor system, and/or one or more components thereof, such as the flow sensor system disclosed in U.S. Pat. No. 9,970,794, which is hereby incorporated by reference in its entirety.

Housing 210 may include interior surface 211*a* and exterior surface 211*b*. Interior surface 211*a* may define interior space 212 of housing 210. Interior space 212 of housing 210 may be fluidically sealed from an external environment by housing 210. For example, exterior surface 211*a* may be exposed to the external environment, while interior space 212 and components (e.g., electronic components, such as a processor, a memory, a bus, a wireless communication device, wiring, and/or the like, audio exciter 150, etc.) located in interior space 212 are sealed off from exposure to any fluids and/or gases that exterior surface 111*a* may be exposed to in the external environment.

In some non-limiting embodiments or aspects, housing 110 may include flat-panel display 216. For example, flat-panel display 216 may form a portion of exterior surface 211*b* of housing 210.

Audio exciter 250 may be connected to (e.g., directly connected to, etc.) interior surface 211*a* of housing 210 and fluidically sealed from the external environment by housing 210. Accordingly, openings or crevices in housing 210 of medical device 200 may be reduced or completely eliminated, while still providing audio output from medical device 200. Moreover, use of a membrane over a speaker, which may include porous openings, may muffle the sound and/or deteriorate over multiple cleanings and time, and/or thin out the housing enough for some sound to penetrate again leading to muffling and/or lower sound volume than desired, may be avoided. In contrast, with audio exciter 250 connected to interior surface 211*a* of housing 210, housing 210 (e.g., the entire housing 210, a face of housing 210, etc.) may produce the audio output by movement of the material of housing 210 itself, with audio exciter 250 sealed within housing 210 with no openings for liquid to ingress during cleaning and with no grates or crevices for material to accumulate within.

In some non-limiting embodiments or aspects, audio exciter 250 may include the ASX02604-R audio exciter and/or the ASX02108-R audio exciter, each of which are manufactured by PUI Audio, Inc.

In some non-limiting embodiments or aspects, audio exciter 250 may be connected to (e.g., directly connected to, etc.) a portion of interior surface 211*a* of housing 210 that includes flat-panel display 216. For example, audio exciter 250 may be directly connected to a rear surface of flat panel display 216 opposite a display side of flat panel display 216. Accordingly, with audio exciter 250 connected to a rear (non-display) side of the flat-panel display, the panel (e.g. a glass panel, etc.) of the display may be displaced by audio exciter 250 in a direction facing a user that is viewing flat-panel display 216 such that sounds is directed at the user.

Figure 2B:
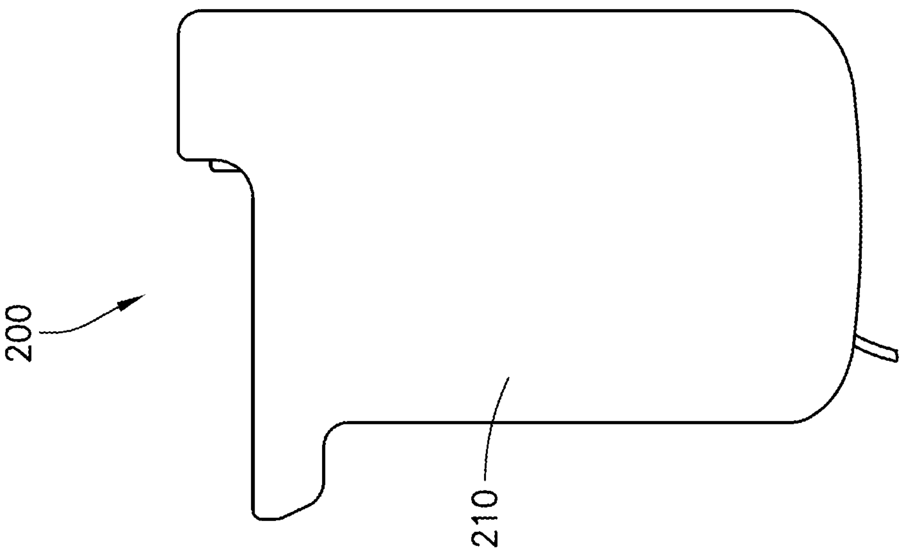
FIG. 2B is a rear view of non-limiting embodiments or aspects of a medical device with audio output for use in a sterile field.
Figure 2A:
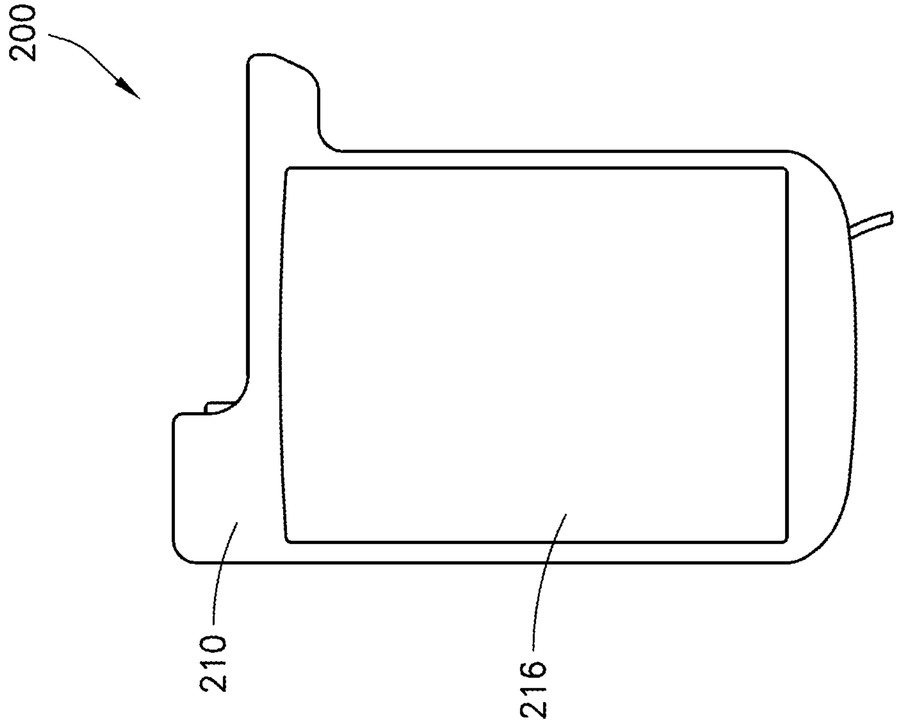
FIG. 2A is a front view of non-limiting embodiments or aspects of a medical device with audio output for use in a sterile field.
Figure 2D:
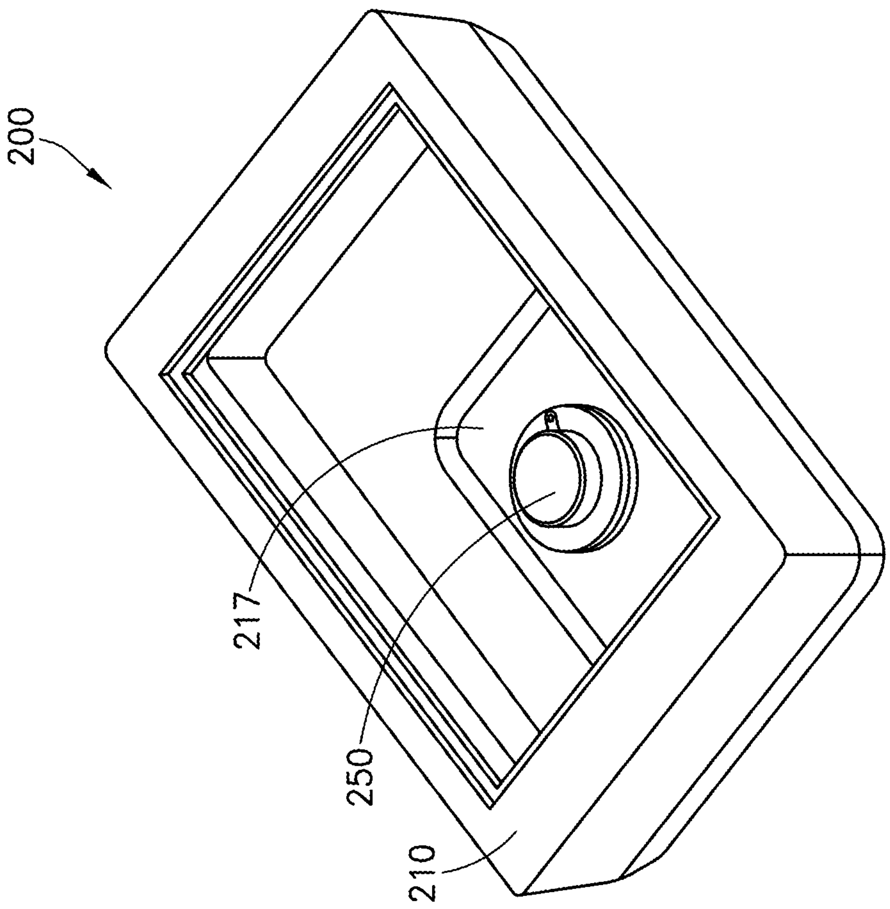
FIG. 2D is a perspective view of non-limiting embodiments or aspects of components of a medical device with audio output for use in a sterile field.
Figure 2C:
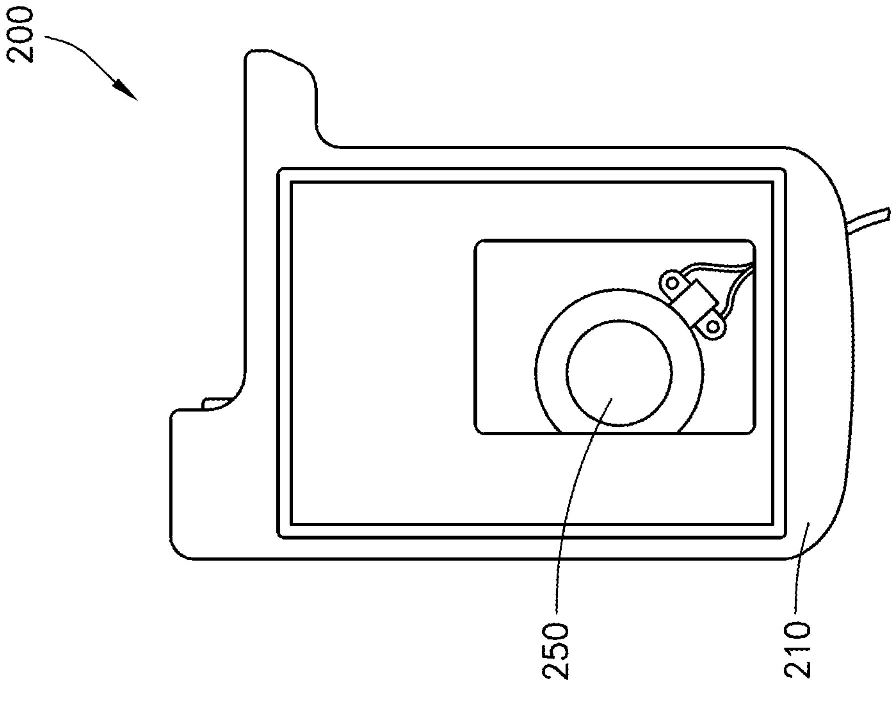
FIG. 2C is an interior view of non-limiting embodiments or aspects of a medical device with audio output for use in a sterile field.
Figure 2E:
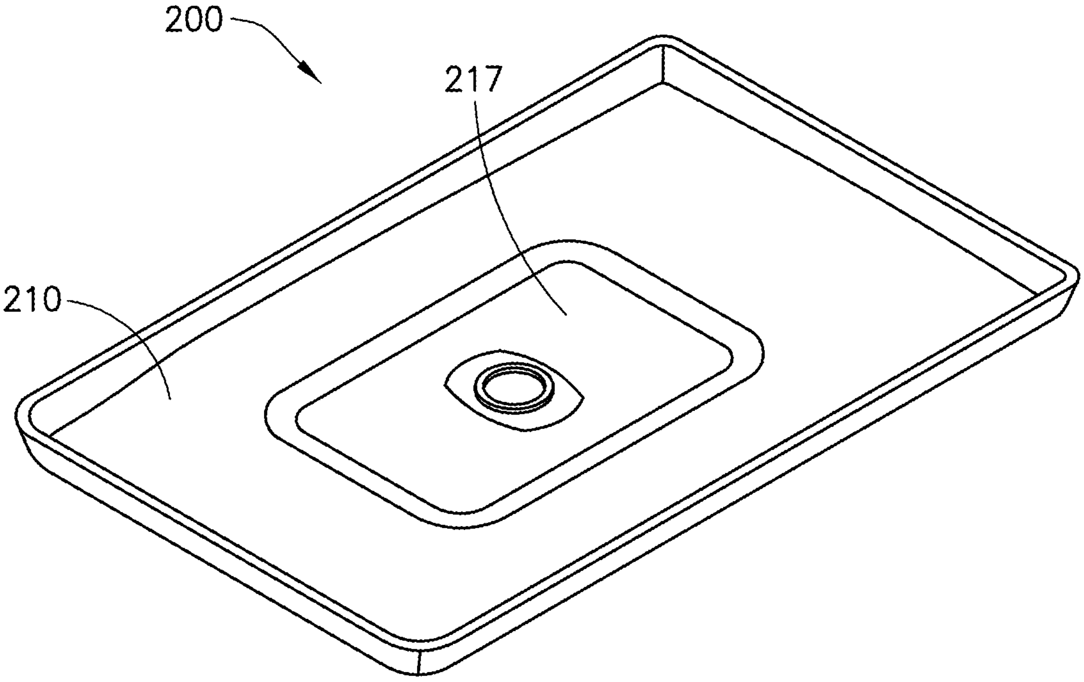
FIG. 2E is a perspective view of non-limiting embodiments or aspects of components of a medical device with audio output for use in a sterile field.
Figure 2F:
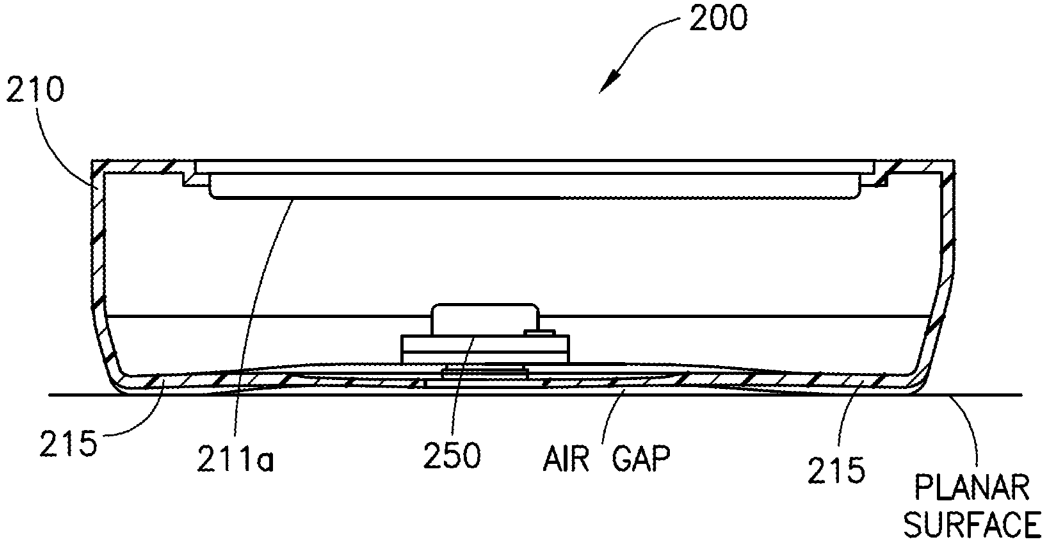
FIG. 2F is a perspective view of non-limiting embodiments or aspects of a medical device with audio output for use in a sterile field.
Figure 2G:
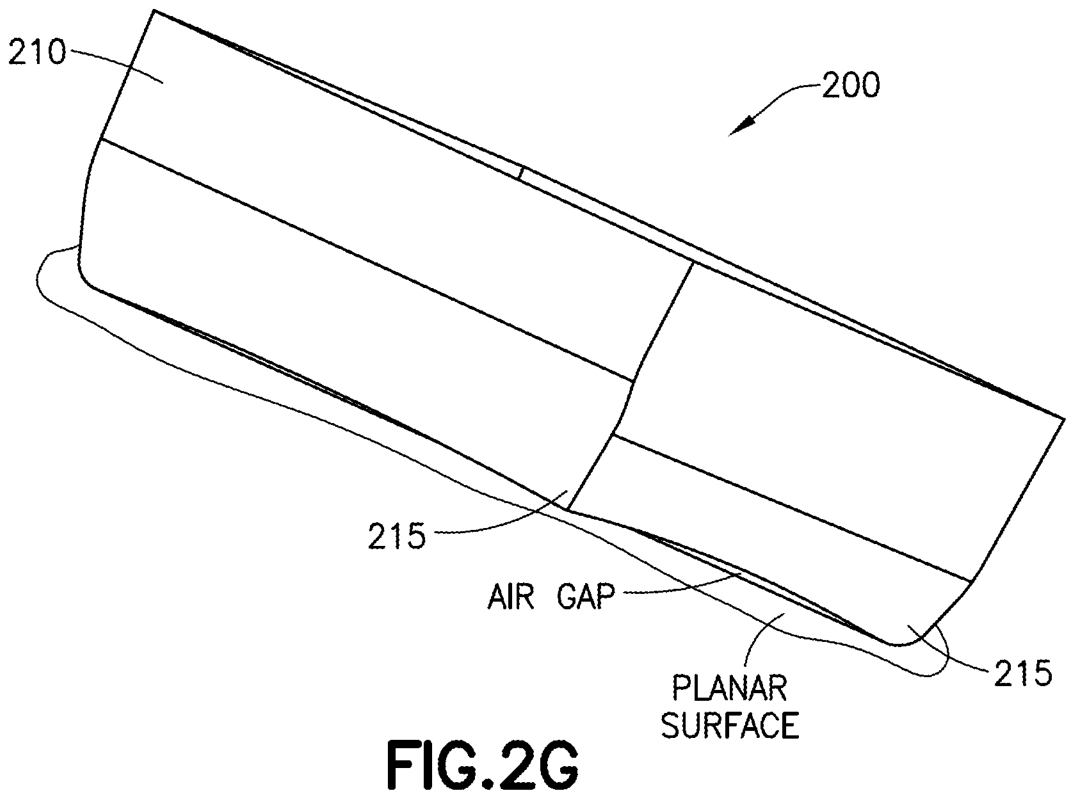
FIG. 2G is a perspective view of non-limiting embodiments or aspects of a medical device with audio output for use in a sterile field.
Figure 2H:
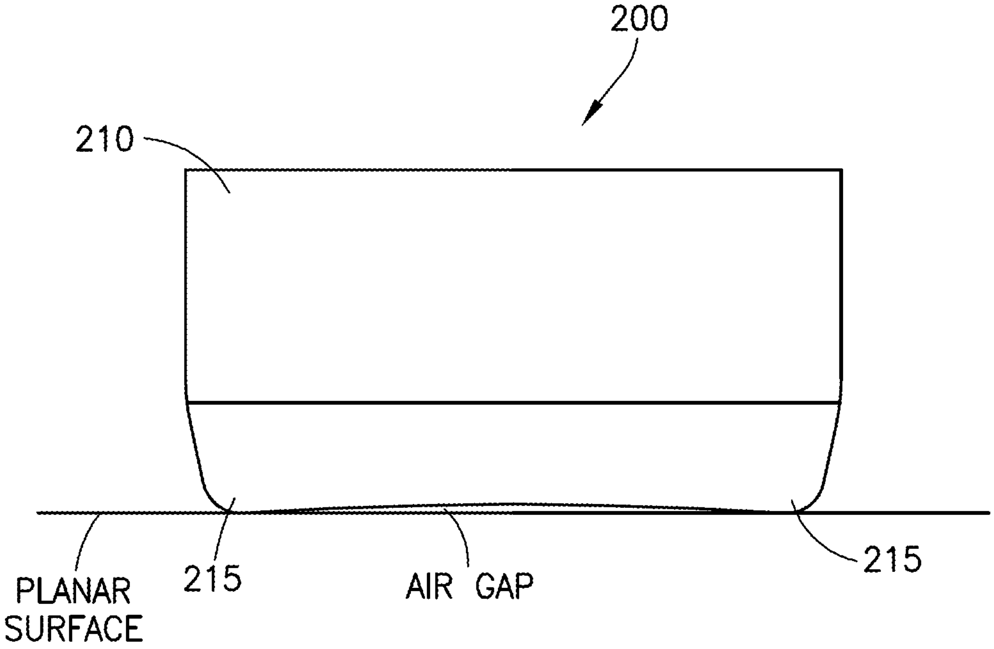
FIG. 2H is a side view of non-limiting embodiments or aspects of a medical device with audio output for use in a sterile field.
Figure 2I:
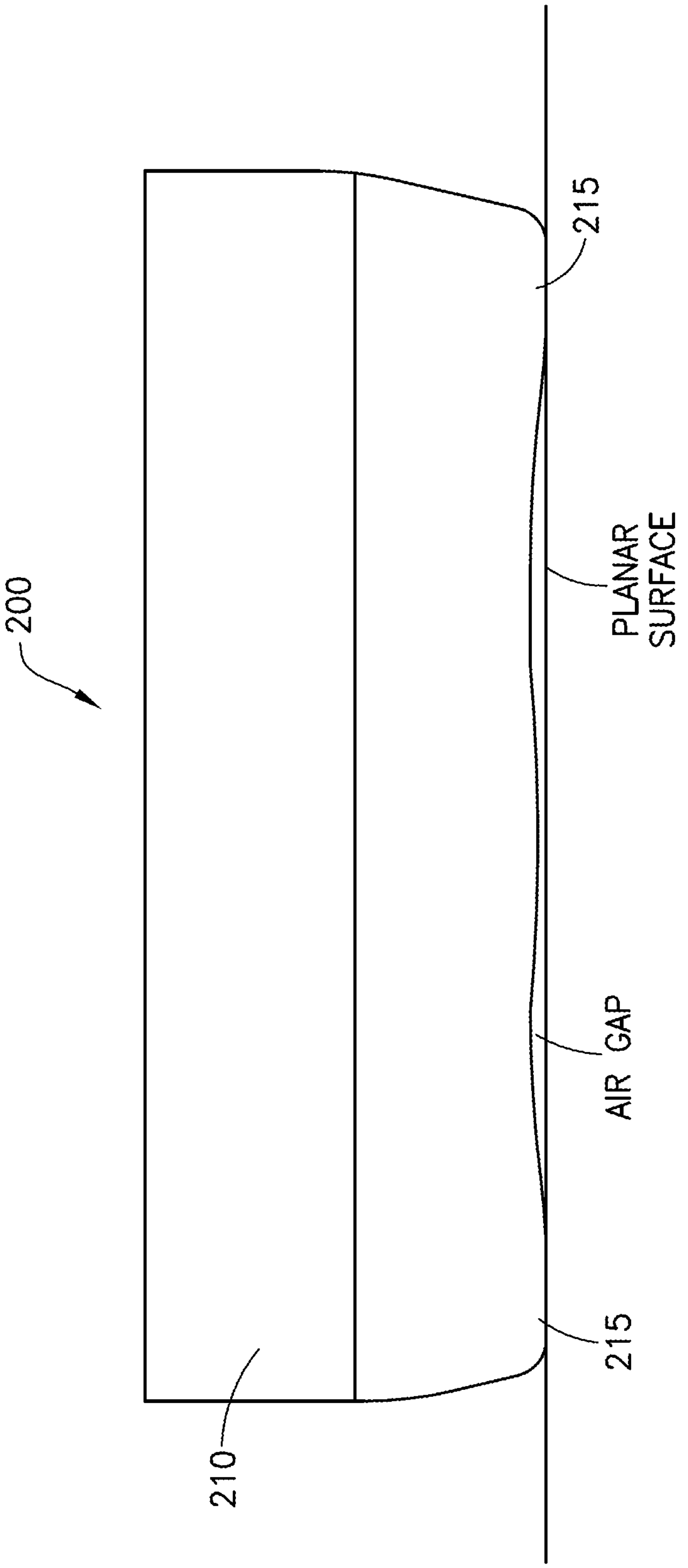
FIG. 2I is a side view of non-limiting embodiments or aspects of a medical device with audio output for use in a sterile field.

In some non-limiting embodiments or aspect, for example, as shown in FIG. 2F, a portion of interior surface 211*a* of housing 210 to which audio exciter 250 is connected may be directly opposite another portion of interior surface 211*a* of housing 210 including flat-panel display 216.

In some non-limiting embodiments or aspects, a portion of exterior surface 211*b* of housing opposite 210 a portion of interior surface 211*a* of housing 210 to which audio exciter 250 is connected may include a plurality of raised portions 215 spaced apart from one another and extending from exterior surface 211*b* of the housing 210. For example, audio exciter 250 may be connected to interior surface 211*a* of housing 210 between the plurality of raised portions 215 extending from exterior surface 211*b* of housing 210. In some non-limiting embodiments or aspects, the plurality of raised portions 215 includes at least three raised portions. For example, FIGS. 2F-2I show non-limiting embodiments or aspects of medical device 200 including four raised portions 215.

Accordingly, the plurality of raised portions 215 may provide clearance between a portion of exterior surface 211*b* of medical device 210 opposite to a portion of interior surface 211*a* to which audio exciter 2450 is attached and a surface (e.g., a planar surface, etc.) on which medical device 200 is placed, which enables audio exciter 250 to displace exterior surface 211*b* without touching the surface on which medical device 210 is placed and improved air movement for sound to escape from under medical device 210 via air gaps. For example, a mass of housing 210 may be supported at outside corners of housing 210, thereby providing a slight elevation above the surface on which medical device 200 is placed to enable sound to escape to provide a desired volume.

In some non-limiting embodiments or aspects, a portion of interior surface 211*a* of housing 210 to which audio exciter 250 is connected may include recess 217 such that a thickness of housing 210 between interior surface 211*a* and exterior surface 211*b* at recess 217 is less than the thickness of housing 210 surrounding recess 217. For example, recess 217 may be located on interior surface 211*a* between the plurality of raised portions 215 extending from exterior surface 211*b* of housing 210.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, any of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A medical device with audio output for use in a sterile field, comprising:

a housing including an interior surface and an exterior surface, wherein the interior surface defines an interior space of the housing, and wherein the housing includes an opening to the interior space of the housing;

a speaker cover in the opening of the housing, wherein the housing and the speaker cover fluidically seal the interior space of the housing from an external environment, and wherein the exterior surface of the housing is exposed to the external environment;

a speaker enclosure connected to the housing; and a speaker frame including a speaker driver in the interior space of the housing between the speaker cover and the speaker enclosure, wherein the interior space of the housing including the speaker frame including the speaker driver is fluidically sealed from the external environment by the housing and the speaker cover, wherein the speaker enclosure includes a base and a sidewall extending from and surrounding the base, wherein the base includes a projection extending from the base in a same direction as the sidewall, and wherein the speaker frame including the speaker driver is connected to the projection.

2. The medical device of claim 1, wherein the base includes a hole.

3. The medical device of claim 2, further comprising:

an adhesive foam between the speaker frame and the projection.

4. A medical device with audio output for use in a sterile field, comprising:

a housing including an interior surface and an exterior surface, wherein the interior surface defines an interior space of the housing, and wherein the housing includes an opening to the interior space of the housing;

a speaker cover in the opening of the housing, wherein the housing and the speaker cover fluidically seal the interior space of the housing from an external environment, and wherein the exterior surface of the housing is exposed to the external environment;

a speaker enclosure connected to the housing; and a speaker frame including a speaker driver in the interior space of the housing between the speaker cover and the speaker enclosure, wherein the interior space of the housing including the speaker frame including the speaker driver is fluidically sealed from the external environment by the housing and the speaker cover, wherein the speaker cover includes a central portion surrounded by a flange, and wherein the flange forms a fluid tight seal with the exterior surface of the housing.

5. The medical device of claim 4, wherein a flange is connected to the exterior surface of the housing via an adhesive to form a fluid tight seal.

6. The medical device of claim 4, wherein a flange includes a flexible material, wherein the speaker frame includes a plurality of tabs of rigid material more rigid than the flexible material and extending from the frame, wherein an underside of the flange is connected to the exterior surface of the housing, and wherein a top surface of the plurality of tabs is connected to the interior surface of the housing.

7. The medical device of claim 1, wherein the speaker enclosure is integrally formed with the housing.

8. The medical device of claim 1, wherein the speaker cover is directly connected to the speaker enclosure.

9. A medical device with audio output for use in a sterile field, comprising:

a housing including an interior surface and an exterior surface, wherein the interior surface defines an interior space of the housing, and wherein the housing includes an opening to the interior space of the housing;

a speaker cover in the opening of the housing, wherein the housing and the speaker cover fluidically seal the interior space of the housing from an external environment, and wherein the exterior surface of the housing is exposed to the external environment;

a speaker enclosure connected to the housing; and a speaker frame including a speaker driver in the interior space of the housing between the speaker cover and the speaker enclosure, wherein the interior space of the housing including the speaker frame including the speaker driver is fluidically sealed from the external environment by the housing and the speaker cover, wherein the housing includes a flat-panel display, and wherein the flat-panel display forms a portion of the exterior surface of the housing.

10. The medical device of claim 1, further comprising:

a flow sensor.

11. A medical device with audio output for use in a sterile field, comprising:

a housing including an interior surface and an exterior surface, wherein the interior surface defines an interior space of the housing, and wherein the interior space of the housing is fluidically sealed from an external environment by the housing; and an audio exciter connected to the interior surface of the housing and fluidically sealed from the external environment by the housing;

wherein a portion of the exterior surface of the housing opposite a portion of the interior surface of the housing to which the audio exciter is connected includes a plurality of raised portions spaced apart from one another and extending from the exterior surface of the housing, and wherein the portion of the interior surface of the housing to which the audio exciter is connected includes a recess such that a thickness of the housing between the interior surface and the exterior surface at the recess is less than the thickness of the housing surrounding the recess.

12. The medical device of claim 11, wherein the audio exciter is connected to the interior surface of the housing between the plurality of raised portions extending from the exterior surface of the housing.

13. The medical device of claim 11, wherein the plurality or raised portions includes at least three raised portions.

14. The medical device of claim 11, wherein the recess is located between the plurality of raised portions extending from the exterior surface of the housing.

15. The medical device of claim 11, wherein the housing includes a flat-panel display, and wherein the portion of the interior surface of the housing to which the audio exciter is connected is directly opposite another portion of the interior surface of the housing including the flat-panel display.

16. A medical device with audio output for use in a sterile field, comprising:

a housing including an interior surface and an exterior surface, wherein the interior surface defines an interior space of the housing, and wherein the interior space of the housing is fluidically sealed from an external environment by the housing; and an audio exciter connected to the interior surface of the housing and fluidically sealed from the external environment by the housing, wherein the housing includes a flat-panel display, and wherein the audio exciter is connected to a portion of the interior surface of the housing including the flat-panel display.

17. The medical device of claim 11, further comprising:

a flow sensor.

* * * * *